United States Patent [19]

Gansow et al.

[11] Patent Number: 5,428,154

[45] Date of Patent: Jun. 27, 1995

[54] COMPLEXES OF FUNCTIONALIZED TETRAAZACYCLODODECANE CHELATES WITH BISMUTH, LEAD, YTRIIUM, ACTINIUM, OR LANTHANIDE METAL IONS

[75] Inventors: Otto A. Gansow, Washington, D.C.; Martin W. Brechbiel, Annandale, Va.; Michael A. Mägerstädt, Hofheim, Germany

[73] Assignee: The United States of America as represented by the Department of Health and Human Services, Washington, D.C.

[21] Appl. No.: 140,714

[22] Filed: Oct. 22, 1993

Related U.S. Application Data

[63] Continuation of Ser. No. 815,956, Jan. 2, 1992, abandoned, which is a continuation of Ser. No. 198,538, May 25, 1988, abandoned.

[51] Int. Cl.$^6$ ............... C07D 251/02; C07D 257/02; C07D 259/00; C07F 5/00; C07F 13/00; C07R 15/00
[52] U.S. Cl. .................... 540/465; 540/452; 540/474; 534/10; 534/14; 534/15; 534/16
[58] Field of Search .................. 540/452, 465, 474; 534/10, 14, 15, 16

[56] References Cited

U.S. PATENT DOCUMENTS

| | | | |
|---|---|---|---|
| 2,186,464 | 10/1939 | Mauersberger | 540/474 |
| 3,860,576 | 1/1975 | Ham et al. | 540/474 |
| 3,979,379 | 9/1976 | Siele | 260/239 |
| 4,174,319 | 11/1979 | Kosuke | 540/474 |
| 4,174,428 | 11/1979 | Tabushi et al. | 540/465 |
| 4,543,213 | 9/1985 | Weitl et al. | 260/239 |
| 4,578,517 | 3/1986 | Johnson et al. | 564/479 |
| 4,678,667 | 7/1987 | Meares et al. | 540/474 |
| 4,702,998 | 10/1987 | Tanaka et al. | 540/452 X |
| 4,885,363 | 12/1989 | Tweedle et al. | 540/465 |
| 4,923,985 | 5/1990 | Gansow | 540/474 |
| 4,987,227 | 1/1991 | Burrows et al. | 540/452 |
| 5,049,667 | 9/1991 | Schaefer et al. | 540/474 |
| 5,053,503 | 10/1991 | Dean et al. | 540/474 |
| 5,064,956 | 11/1991 | Kruper | 540/474 |
| 5,087,696 | 2/1992 | Parker et al. | 540/465 |
| 5,132,409 | 7/1992 | Felder et al. | 534/10 |

FOREIGN PATENT DOCUMENTS

| | | | |
|---|---|---|---|
| 7621787 | 2/1988 | Australia | 540/474 |
| 1529150 | 10/1978 | United Kingdom | 260/239 |

OTHER PUBLICATIONS

Tsuboyama, et al., *Tetrahedron Lets.*, No. 16, Pergamon, 1970 pp. 1367–1370.

*Primary Examiner*—Floyd D. Higel
*Attorney, Agent, or Firm*—Leydig, Voit & Mayer, Ltd.

[57] ABSTRACT

The invention is a chelate of formula I:

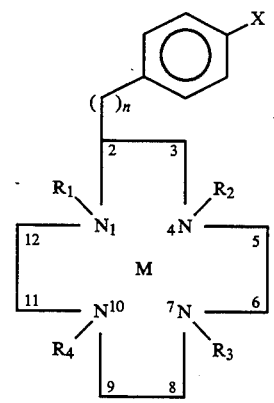

wherein
$R_{1-4}$ is —CH$_2$COOH;
n is 1 to 5;
X is a member selected from the group consisting of
 —NO$_2$,
 —NH$_2$,
 —NCS,
 —NHCOCH$_2$—Z, with Z being a member selected from the group consisting of Br and I,
 —COOH; and
 —OCH$_2$OOCH;

(Abstract continued on next page.)

and M is a metal ion selected from the group of elements consisting of

Bi, Pb, Y, Cd, Hg, Al, Th, Sr, and Lanthanides.

The invention also includes a chelate, wherein M is a copper ion and n is an integer from 2 to 5. The invention includes chelate conjugates of formula I and ligand conjugates of formula II:

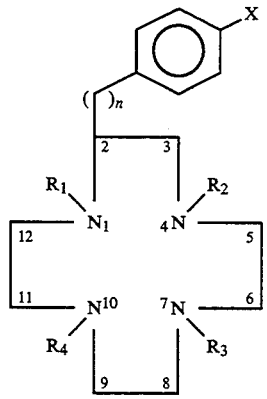

The invention also includes methods to use these compounds for treatment of cellular disorders and for diagnostic tests.

8 Claims, No Drawings

COMPLEXES OF FUNCTIONALIZED TETRAAZACYCLODODECANE CHELATES WITH BISMUTH, LEAD, YTRIIUM, ACTINIUM, OR LANTHANIDE METAL IONS

This is a continuation of application Ser. No. 07/815,956 filed on Jan. 2, 1992, now abandoned which is, in turn, a continuation of Ser. No. 07/198,538 filed on May 25, 1988, now abandoned.

BACKGROUND OF THE INVENTION

1. Field of the Invention

This invention relates to macrocyclic chelates and methods of use thereof. More specifically, this invention relates to 2-substituted 1,4,7,10-Tetraaza cyclododecane-N,N'',N''N'''-tetraacetic acid, 2-substituted 1,4,7,10-Tetraazacyclododecane, and analog macrocycles and their uses.

2. Description of the Background Art

Macrocycles have been studied for their usefulness as chelates for numerous metal ions that have therapeutic, diagnostic, or other uses. A macrocycle of particular usefulness as a chelate is the 1,4,7,10-Tetraazacyclododecane-N,N',N'',N'''-tetraacetic acid (DOTA). DOTA compounds have been linked to biomolecules to form delivery systems for the chelated metal ion to specific sites within an organism.

U.S. Pat. No. 4,678,667 to Meares et al. discloses a macrocyclic, bifunctional chelating agent. The chelating agents of this disclosure can include a DOTA compound that is a Cu(II) chelate. The usefulness of the chelating agent is limited to the effects of the copper metal ion. The synthesis of this disclosure gives low and not always reproducible results.

U.S. Pat. No. 4,622,420, an earlier patent to Meares et al., disclosed bifunctional chelating agents of the acyclic ligand, ethylene diamine N,N'N'',N''' tetraacetic acid (EDTA), useful for binding metals other than copper, such as Indium. These compounds are useful for imaging of tumors.

U.S. Pat. No. 4,652,519 to Warshawsky et al. discloses bifunctional chelating agents and process for their production. The compounds disclosed in this patent are analogues of EDTA. These compounds are used to chelate metal ions and are linked to haptens to provide specific site selection within an organism. The compounds of this patent are offered to provide an improved substituent for the EDTA compounds, such as those disclosed in the Meares et al. patent discussed above.

U.S. Pat. Nos. 4,454,106 and 4,472,509 to Gansow et al. disclose the use of metal chelate-conjugated monoclonal antibodies and the specific metal chelate-conjugated monoclonal antibodies. These disclosures provide compounds and methods for treating cellular disorders. Radiometal chelate-conjugated monoclonal antibodies specific to a target cell are used to deliver alpha, beta, or Auger electron-emitting metal ions. These disclosures are not related to DOTA compounds.

The value of having a ligand conjugate to chelate metal ions for therapeutic, diagnostic, and other uses is of commercial importance. This commercial importance is created by the fact that many metal ions have desirable characteristics for these various uses, but the delivery systems for the metal ions lack specificity to target cells or do not adequately bind the metal ions. Examples of the usefulness of specific metal ions are as follows.

The usefulness of radionuclide materials in cancer therapy is disclosed in the article, Kozak et al., "Radionuclide-conjugated monoclonal antibodies: A Synthesis of Immunology, in Organic Chemistry and Nuclear Science," Trends in Biotechnology 4(10):259–264 (1985). This article discusses the use of antibody conjugates to deliver either alpha or beta radiation. The value of alpha radiation from bismuth-212 in radionuclide therapy is further discussed in the two articles, Kozak et al., "Bismuth-212-labeled anti-Tac monoclonal antibody: Alpha-particle-emitting Radionuclides as Modalities for Radioimmunotherapy," Proc. Natl. Acad. Sci. U.S.A 83:474–478 (1986) and Gansow et al., "Generator-produced Bi-212 Chelated to Chemically Modified Monoclonal Antibody for Use in Radiotherapy" Am. Chem. So. Symposium Series 15:215–227 (1984).

Examples of other uses for chelated metal ions are disclosed in the following articles. Magerstadt et al., "Gd(DOTA): An Alternative to Gd(DPTA) as a $T_{1,2}$ Relaxation Agent for NMR Imaging or Spectroscopy," Magnetic Resonance in Medicine 3:808–812 (1986), discloses the usefulness of gadolinium as a relaxation agent for NMR imaging. The article, Spirlet et al., "Structural Characterization of a Terbium(III) Complex with 1,4,8,11-Tetraazacyclotetradecane-1,4,8,11-tetraacetic Acid. Lanthanide Ions and the Conformation of the 14-Membered Macrocyles," Inorganic Chemistry 23(25):4278–4283 (1984), discloses the usefulness of lanthanide chelates.

The industry is lacking a DOTA chelate that can be efficiently produced in high yields and that has desirable chelating qualities for numerous metal ions.

SUMMARY OF THE INVENTION

The invention is a chelate of formula

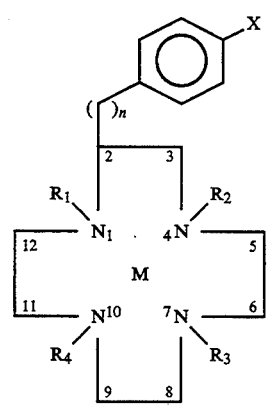

wherein
$R_{1-4}$ is —$CH_2COOH$;
n is 1 to 5;
X is a member selected from the group consisting of
—$NO_2$,
—$NH_2$,
—NCS,
—$NHCOCH_2$—Z, with Z being a member selected from the group consisting of Br and I,
—COOH,
—$OCH_2COOH$;
and M is a metal ion being a member selected from the group of elements consisting of Bi, Pb, Y, Cd, Hg, Ac, Th, Sr, and Lanthanides.

The invention can include a chelate, wherein M is a copper ion and n is an integer from 2 to 5. The invention includes chelate conjugates of formula I and ligand conjugates of formula II:

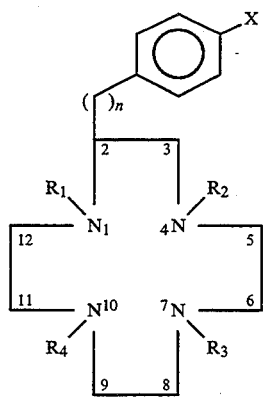

The invention also includes methods to use these compounds for treatment of cellular disorders and for diagnostic tests.

Table I provides herein illustrates a chemical pathway to produce the preferred embodiment of the invention.

DETAILED DESCRIPTION OF THE INVENTION

The compound of this invention is a substituted DOTA represented by formula I, shown above or specifically by compound X in Table I, below. Compound X can subsequently be converted to other substituted DOTA compounds, but compound X is the parent compound for such other compounds. The general formula is a 12 membered ring tetraaza macromolecule with the nitrogens in the 1, 4, 7, and 10 positions. Each of the nitrogens is "ribbed" by an ethylene group.

The substituted DOTA ligand represented by compound X in Table I complexes metals. Metal complexes are formed by placing the DOTA into solution with an appropriate metal salt containing the metal to be chelated. Metal salts have to be selected so as to prevent the hydrolysis of the metal. Also, reaction conditions in an aqueous medium have to be chosen such that the metal is not hydrolyzed. For example, a lead nitrate complex, bismuth iodide complex, or yttrium acetate salts can be used to form a metal chelate with lead, bismuth, or yttrium, respectively. General examples of suitable salts include any soluble divalent metal complex or any trivalent metal complex that is not hydrolyzed at pH 4 or below. Thorium requires the use of iodide salt, specifically. The most desirable metal ions for chelation with formula I are members from the group consisting of bismuth, lead, yttrium, cadmium, mercury, actinium, thorium, strontium, and any of the elements of the lanthanide elements. The most desirable elements of the lanthanide series are gadolinium, for use in NMR imaging and as a relaxation agent in NMR imaging, and terbium and europium, because of their use as chromophores in time-resolved fluorescence spectroscopy. These fluorescent compounds can be useful in an in vitro diagnostic assay, where a fluorescent assay is used, rather than a radioactive amino assay.

The X substituent of formula is desirably a substituent that conjugates the compound with haptens. This substituent is desirably a free-end nitro group, which can be reduced to an amine. The amine can then be activated with a compound, such as thionyl chloride, to form a reactive chemical group, such as an isothiocyanate. An isothiocyanate is preferred because it links directly to amino residues of a hapten such as a monoclonal antibody. The aniline group can be linked to an oxidized carbohydrate on the protein and, subsequently, the linkage fixed by reduction with cyanoborohydride. The amino group then can also be reacted with bromoacetyl chloride or iodoacetyl chloride to form —NHCOCH$_2$Z with Z being bromide or iodide. This group reacts with any available amine or sulfhydryl group on a hapten to form a stable covalent bond. If tyrosine is used in the formulation of the macromolecule, a carboxylic acid or methoxy carboxylate group can be in this position of the compound. The most desirable substituents for this position are members selected from the group consisting of —NO$_2$, —NH$_2$, —NCS, —COOH, —OCH$_2$COOH, —OCH$_2$COOH, and —NHCOCH$_2$—Z, with Z being a member selected from the group consisting of bromide and iodide. The preferred substituent for this position is —NCS.

The haptens suitable for linking with the substituent at the X position of formula I can vary widely. The most desirable haptens are members selected from the group consisting of hormones, steroids, enzymes, and proteins. These haptens are desirable because of their site specificity to tumors and/or various organs of the body. The preferred hapten for use in treating cellular disorders or various disease conditions is a monoclonal antibody.

The compound of this invention can have n equal an integer from 1 to 5. In the preferred embodiment, M equals 2. It is desirable for n to equal 2 versus 1 because the chelating ligand is further separated from the antibody and has more rotation. The increased free rotation allows a metal to chelate with the macromolecule more easily. When n is 3 or greater, the synthesis of the compound becomes lengthy.

Table I illustrates the preferred reaction pathway or process for forming the compound of this invention. This reaction results in a compound of formula I, wherein n is 1. If n is to equal 2, an additional methylene group would be present between the alpha amino carbon and the aromatic group. This compound is 2-amino-4-nitrophenylbutyric acid.

TABLE I

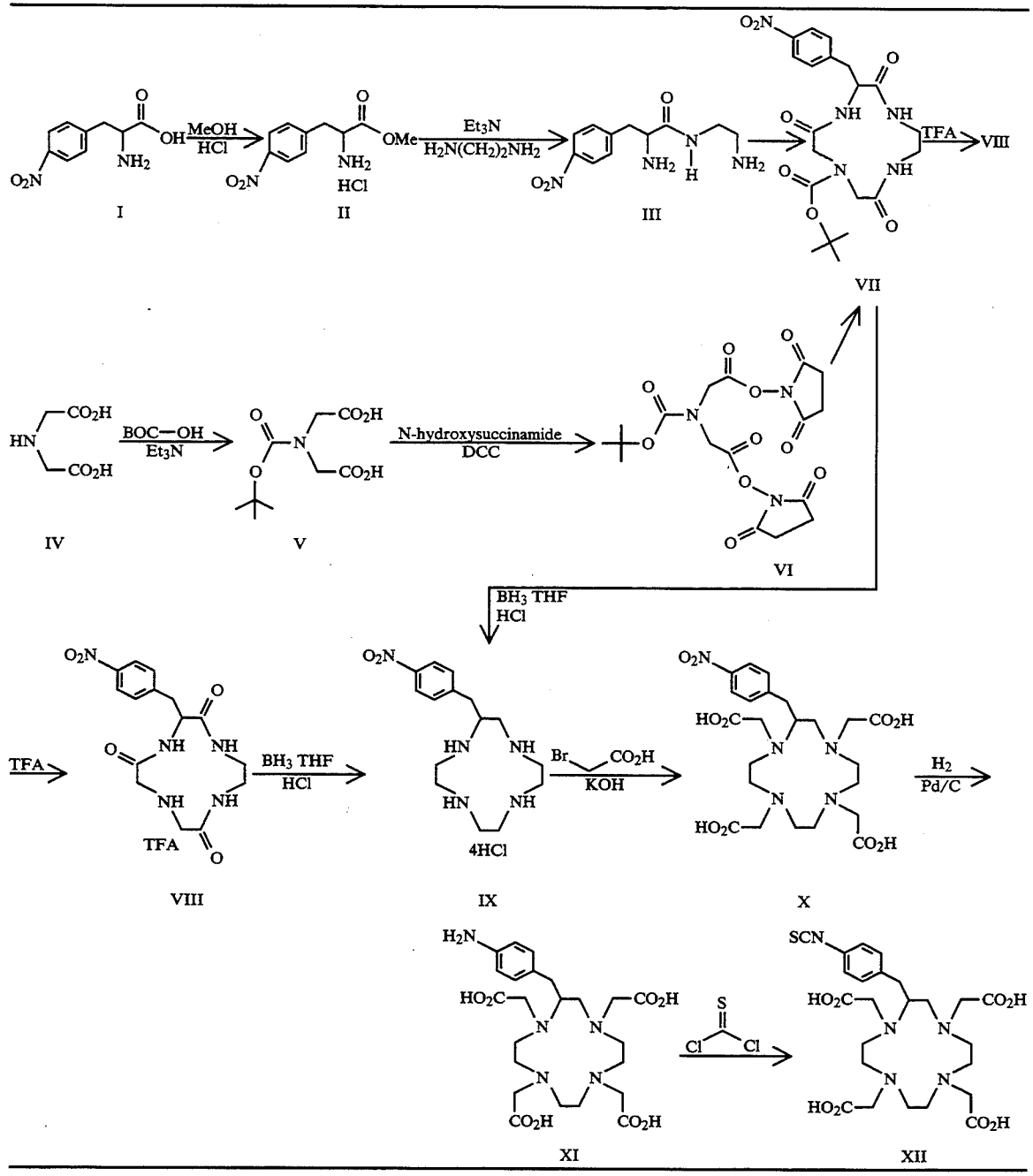

The process for synthesizing a compound according to this invention first provides a triamine with a substituent is in the 2-position. The embodiment of Table I has a methylene [n=1] as the initial substituent for linkage. The preferred embodiment has a phenyleythylene group. The process then provides a tetraaza macromolecule having the substituent in the 2 position. Alkylation with bromoacetic acid forms the four carbon to nitrogen bonds of the carboxymethylene substituents at the R1, R2, R3 and R4 in formula I.

The process shown in Table I reacts p-nitrophenyl alanine with methanol and hydrochloric acid to form the ester compound II. This ester is reacted with ethylenediamine in the presence of triethylamine to remove the hydrochloride salt of the ester formed in compound II. The condensate of the amide of the ethylenediamine adduct or compound III is subsequently reacted with a diactive ester or compound VI to form a cyclic product or compound VII.

The desired diactive ester VI is formed sequentially from amidodiacetic acid for IV of Table 1. The amine is first blocked by using the reagent BOC—ON or any other suitable blocking agent, such as FMOC, in the presence of triethylamine which serves to deprotonate the starting material. The subsequent nitrogen-blocked diacetic acid V or other such nitrogen blocked compound is then coupled to N-hydroxysuccinimide, or any other suitable compound, such as phenols, or N-hydroxydicarboximides which forms a reactive ester. The choice of compounds which form active esters or blocking groups is within the scope of the art. The coupling is done by dicyclohexylcarbodiimide or "DCC". This step produces the nitrogen-blocked active ester or compound VI.

Ring formation under high dilution conditions between amino acidamide or compound III with the nitrogen-blocked active ester of compound VI then occurs. This condensing step forms the triamide macrocycle or compound VII. Compound VII is produced in very high yield. The yield is typically at least about 80 percent. The yield more desirably is between about 80 percent to about 95 percent.

The synthesis of the macrocycle of compound VII may be accomplished by two pathways. Th amine nitrogen of compound VII is deblocked with trifluoroacetic acid or "TFA". This forms the TFA salt of the triamide macrocycle or compound VIII. This compound is reduced with borane/petrahydrofuran or THF. The resulting borane adduct is cleaved by hydrochloric acid to form the substituted tetraazamacrocycle of compound IX. This tetraazamacrocycle can then be alkylated with haloacetic acid in the presence of base to form a nitrobenzyl DOTA or compound X. Alternatively, compound VII can be reduced with borane/THF and reacted with hydrochloric acid to form compound IX directly. This alternative pathway produces slightly poorer yields.

The nitro group of compound X can be reduced with hydrogen over platinum on a carbon catalyst to produce the amino group or the aminobenzyl DOTA depicted as compound XI. Compound XI can then be reacted with thiophosgene to produce the isothiocyanate or compound XII.

The methodology in column 3 of U.S. Pat. No. 4,652,519 to Warshawsky et al., hereby incorporated by reference, provides the methodology to produce the —COOH substituent. This procedure produces the ethylene diamine intermediate. The desired intermediate macrocycle is produced by forming the analogous diactive ester of compound VI by using N,N'-ethylenediamine-diacetic acid. Condensation of the diamine with the dinitrogen, diBOC diactive ester produces a diamide intermediary, which is reduced by diborane to produce the appropriate tetraaza macrocycle. The DOTA ligand can be made from this macrocycle. The synthesis of the X and Z groups are also disclosed by the Warshawsky et al. patent.

The reaction steps described above to produce compounds X, XI, and XII are known. The novel feature of the process provided in Table I is the cyclization procedure. The conversion reaction of compound IV with compound VI to form the macrocycle and the full reduction of the macrocycle to produce compound X produces the unexpected results of very high yields compound X.

In its preferred embodiment the coupling of an isothiocyanate chelate of compound XII of Table I is done by direct conjugation of the isothiocyanate with a free amino group found in many residues of proteins, enzymes or other compounds, such as certain hormones. An example of this situation with a hormone is found with the free amino group provided by the epsilon amino group of the lysine or the terminal amino group as the hormone peptide chain. Any free amino group can react with the isothiocyanate to form a thiourea linkage, which is covalently coupled and irreversible. The use of a steroid as a hapten requires that an amino function be present in the steroid.

An advantage of the amine derivative chelate of compound XI of Table I is that, when coupling to proteins and, in particular, when coupling to antibodies, the carbohydrate of the antibody can be oxidized prior to the coupling reaction. The amine reacts with the aldehyde that is formed on the protein. This aldimine formed can be reduced by cyanoborohydride to form a covalent secondary amine linkage to the antibody in a position that is site-specific. This position is away from the binding site of the FAB'2 part of the monoclonal antibody.

A desirable embodiment of the invention is one having copper metal ion, n is an integer from 2 to 5. This embodiment of the invention can be used to label a monoclonal antibody with $Cu^{67}$. When n is an integer from 2 to 5, there is less hindrance of the chain of the ligand with the protein than occurs when n is 1. When n is an integer from 2 to 5, sufficient space is provided between the ligand and the protein to allow freer rotation of the ligand. This results in more efficient chelation of the copper ion by the resulting conjugate.

An embodiment of the invention involves a ligand-hapten conjugate of formula II:

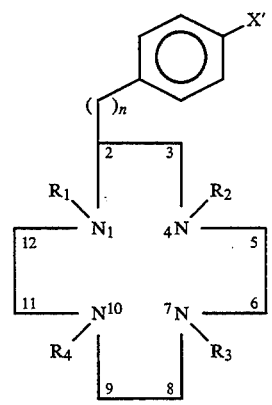

This conjugate chelates metal ions. It is desirable to expose many metals to the protein conjugate in a concentrated metal solution for as short a period of time as possible. Certain metals, such as divalent metal ions, react rapidly and directly with the conjugate. The kinetics of the formation reactions for these compounds are so rapid that it is desirable to have the ligand-hapten conjugate available in the pharmacy immediately prior to use. The conjugate can then be mixed in the radionuclide to form a complex and, subsequently, the metal chelate conjugate formed can be purified by, for example, size exclusion high pressure liquid chromatography. A desirable hapten for the ligand conjugate can be selected from the group consisting of hormones, steroids, enzymes, and proteins.

The most commercially useful embodiments of the invention are chelate conjugates having formula I, wherein (1) n is an integer from 1 to 5, (2) X' is a member selected from the group consisting of —NHQ, —NCS—Q, —NHCOCH$_2$—Q, —OCH$_2$COOQ, and —COO—Q, with Q being a hapten selected from the group consisting of hormones, steroids, enzymes, and proteins, and (3) M is a metal ion being a member selected from the group of elements consisting of Bi, Pb, Y, Cd, Hg, Ac, Th, Sr, and Lanthanides. These chelates conjugates can deliver radioactive metal ions, such as $Pb^{212}$, $Bi^{212}$, $Y^{90}$, $Th^{224}$, and $Sr^{90}$, to specific cellular disorders.

The preferred embodiment of the invention uses a chelate conjugate binding $Pb^{212}$. $Pb^{212}$ is a very desirable pharmaceutical compound for delivering both beta and alpha radiation to a selected site for treatment of the cellular disorders. The delivery is made through the $Pb^{212}$ ion, which converts with a $10\frac{1}{2}$ hour half-life into $Bi^{212}$. $Bi^{212}$ and daughters deliver one alpha particle per $Pb^{212}$ nucleus. The desirable result of this chelate conjugate is that the $Pb^{212}$ half-life is sufficient to allow site selection from the body fluid by the hapten before the alpha particle is emitted.

The invention includes a process for treating cellular disorders. This process uses the chelate conjugate with a hapten having a selective binding site at the cellular disorder. For example, Q can be a monoclonal antibody, wherein the antibody is directed and created against an epitope found specifically on the tumor cells. Thus, when $Pb^{212}$ is transported to the antegen site and, subsequently, decays in secular equilibrium to $Bi^{212}$ and its daughters, a beta irradiation is produced from the lead disintegration. A beta radiation is produced by the bismuth daughters. This beta radiation is similar to the beta radiation from $Y^{90}$ but, in addition each disintegration of bismuth also produces an alpha particle. In this manner, a radiotherapy is provided with a radiation dose from both an alpha and a beta particle. If desired, only $Bi^{212}$ can be introduced in those cases where the disorder to be treated, such as with leukemic cells, can be easily reached within the 1 hour half-life of $Bi^{212}$. It is also possible to use this method to treat cancers, where the cells are widely differentiated. This might be preferred where only a long-range beta emitter, such as $Y^{90}$, is desired. In differing environments, in vivo, the $Bi^{212}$ is retained inside the chelate after the beta emission in differing amounts. Most desirably, at least 95 percent of $Bi^{212}$ remains in the chelate. In an acidic medium, such as the stomach, at least about 70 percent of the $Bi^{212}$ is retained. Retaining at least about 80 or 90 percent, $Bi^{212}$ is also desirable depending on the medium.

The invention includes a process for diagnostic testing. This process uses a chelate conjugate having formula I, wherein M is a member selected from the group consisting of $Pb^{203}$, $Tc^{99m}$, $In^{111}$, $Ga^{67}$, $Ga^{68}$, $Sc^{43}$, $Sc^{44}$, $Fe^{52}$, $Fe^{54}$, $FE^{56}$, $Fe^{57}$, $Fe^{58}$, and $Co^{55}$. The usefulness of metal ions with both in vitro and in vivo diagnostic procedures is disclosed in U.S. Pat. No. 4,454,106, hereby incorporated by reference.

The most desirable embodiment of this diagnostic process uses $Pb^{203}$. $Pb^{203}$ has a 52.1 hour half-life as a gamma-emitter. $Pb^{203}$ has a unique property in that it decays at a high percentage only by a single photon emission. This gamma emission is preferred and dominant over all other emissions. This single photon emission makes $Pb^{203}$ useful for single photon emission computed spectroscopy [SPECT], which is a diagnostic tool. Thus, when $Pb^{203}$ is linked by use of the chelate to a hapten, which specifically localizes in a tumor, then that particular localization can be three dimensionally mapped for diagnostic purposes in vivo by single photon emission tomography. Alternatively, the emission can be used in vitro in radioimmunoassays.

EXAMPLE 1

The procedures and reagents described above for the preferred embodiment of making the compounds are used for this example.

The antibody specific for the IL-2 antigen is the monoclonal antibody alpha-Tac. This antibody is labelled with the chelate of compound XII of FIG. 1 as follows. The antibody is suspended in a buffered normal saline solution having a pH of about 8.5. Solid ligand or compound XII is added to the protein suspension. The protein conjugate forms during reaction overnight and is purified by dialysis against metal-free 0.05 molar citrate/0.15 molar sodium chloride buffer at pH 5.5. Before labelling with metal, the protein is dialyzed against a solution comprising 0.02 molar N-morpholinoethanesulfonic acid and 0.02 molar acetate at pH 5.9.

The protein in solution is labelled with $Y^{90}$ by reacting with an acetate solution of the isotope followed by passage through a TSK 3000 size exclusion column. This is a high pressure liquid chromotography procedure. The compound is mixed with a pharmaceutical excipient and is used in mammals in a therapeutic amount to treat adult T-cell leukemia in mammals. T-cell leukemia is characterized by extraordinarily large amounts of IL-2 receptors on the tumor cells. The antibody localizes specifically to these tumor cells to deliver its radiation.

EXAMPLES 2 and 3

The procedures and reagents described above for the preferred embodiment of making the compounds are used for these examples. The only difference between Example 1 and Examples 2 and 3 are the use of the antibody B72.3, which binds specifically to a glycoprotein on LS-174T cells. This glycoprotein is also in humans who have colon cancer. The model system of this example is an athymic mouse, into which has been implanted LS-174T cells to develop a tumor on the flank of the animal where the cells were implanted. The diagnostic method used to visualize the growing tumor involves the following components. The chelate of compound 12 is first coupled to gadolinium or $Pb^{203}$ by mixture of the chelate solution at pH 4 to 5 with gadolinium or $Pb^{203}$ nitrate. This material can then be linked directly to the antibody by mixture to react with the protein and purified according to the method of the previous example.

In Example 2, the gadolinium chelate ligand-protein conjugate is injected or introduced into body fluids of a mammal. The gadolinium then localizes along with the antibody to the tumor and conventional resonance magnetic imaging techniques are used to visualize the tumor.

In Example 3, $Pb^{203}$ is used and the metal-labeled protein conjugate is similarly introduced into the mammal, but gamma camera or SPECT imaging is used to visualize the tumor.

What is claimed is:

1. A chelate of formula I:

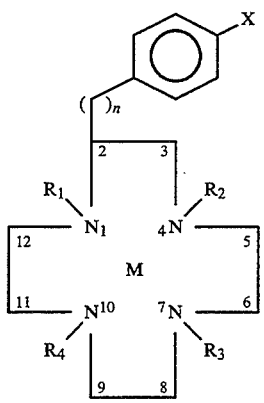

wherein $R_{1-4}$ is —$CH_2COOH$;

wherein n is an integer from 1 to 5;

X is a member selected from the group consisting of
—$NO_2$,
—$NH_2$,
—NCS,
NHCO$CH_2$—Z, with Z being a member selected from the group consisting of Br and I,
—$OCH_2COOH$, and
—COOH;

and M is a metal ion being a member selected from the group of elements consisting of Bi, Pb, Y, Ac, and Lanthanides.

2. The chelate of claim 1, wherein n is 1 to 2 and X is a member selected from the group consisting of —$NO_2$, —NCS, and —NHCO$CH_2$—Z, with Z being a member selected from the group consisting of Br and I.

3. The chelate of claim 2, wherein M is a member selected from the group consisting of Bi, Pb, Y, Th, Sr, Gd, Eu, and Tb.

4. The chelate of claim 1, wherein n is 2, X is —NCS, and M is a member selected from the group consisting of $Pb^{212}$, $Pb^{203}$, $Bi^{212}$, $Y^{90}$, $Th^{224}$, and $Sr^{90}$.

5. The chelate of claim 3, wherein M is a member selected from the group consisting of Pb and Bi.

6. The chelate of claim 2, wherein n is 2, X is NCS, and M is a member selected from the group consisting of Eu, Tb, and Gd.

7. The chelate of claim 1, wherein M is a radioisotope of bismuth.

8. The chelate of claim 7, wherein M is an α-emitting radioisotope of bismuth.

* * * * *